US007815718B2

(12) United States Patent
Yuan et al.

(10) Patent No.: US 7,815,718 B2
(45) Date of Patent: Oct. 19, 2010

(54) AUTOMATED PARTICLE COLLECTION OFF OF FAN BLADES INTO A LIQUID BUFFER

(75) Inventors: Bob Yuan, Belmont, CA (US); Chun-Wah Phil Lin, Hayward, CA (US)

(73) Assignee: MicroFluidic Systems, Inc., Fremont, CA (US)

(*) Notice: Subject to any disclaimer, the term of this patent is extended or adjusted under 35 U.S.C. 154(b) by 1091 days.

(21) Appl. No.: 11/509,878

(22) Filed: Aug. 24, 2006

(65) Prior Publication Data

US 2008/0047429 A1 Feb. 28, 2008

(51) Int. Cl.
*B01D 47/00* (2006.01)

(52) U.S. Cl. ............................ 95/218; 96/282; 96/413; 73/863.22

(58) Field of Classification Search .................. 95/218; 96/281-285, 359; 73/863.12, 863.23, 864.34, 73/863.21, 863.22, 28.05
See application file for complete search history.

(56) References Cited

U.S. PATENT DOCUMENTS 3,651,524 A * 3/1972 Bengtsson et al. ............. 4/211
5,344,085 A * 9/1994 Hofseth ................... 241/46.02
5,934,869 A * 8/1999 Janisse .................... 415/121.3
6,146,591 A * 11/2000 Miller ......................... 422/65
6,267,016 B1 * 7/2001 Call et al. ................ 73/863.22
6,905,885 B2 * 6/2005 Colston et al. .............. 436/518
6,951,147 B2 * 10/2005 Call et al. ................ 73/863.22
7,552,503 B2 * 6/2009 Wakao et al. ................. 15/302
2003/0177750 A1 * 9/2003 Limmer ....................... 57/300
2003/0230152 A1 * 12/2003 McGill et al. ............ 73/864.34
2006/0257853 A1 * 11/2006 Herman ........................ 435/5

* cited by examiner

*Primary Examiner*—Duane Smith
*Assistant Examiner*—Ives Wu
(74) *Attorney, Agent, or Firm*—Haverstock & Owens LLP

(57) ABSTRACT

Fan blades within a fan assembly are rotated in a first rotational direction, thereby generating airflow from above the fan blades downward past the fan blades. Airborne particles adhere to the surface of the fan blades as the air flows past. The fan direction is then reversed maintained at a relatively low rotational rate. A fluid is dispensed onto the hub of the fan blades. Due to the centripetal force of the spinning fan blades, the fluid is spread thin across the top surface of the fan blades and the liquid film washes the blade of the fan, removing particulates from the fan blade. The solution is pushed outward against the inner wall of the fan housing forming a fluid meniscus. The fan speed is increased to push the fluid meniscus into an annular reservoir. The collected fluid is then vacuumed and consolidated into the collection vessel.

25 Claims, 8 Drawing Sheets

```
┌─────────────────────────────────────────────────────────┐
│ Rotate the Fan Blades in the First Rotational Direction │─100
└─────────────────────────────────────────────────────────┘
                            ↓
┌─────────────────────────────────────────────────────────┐
│          Collect the Particles on the Fan Blades        │─110
└─────────────────────────────────────────────────────────┘
                            ↓
┌─────────────────────────────────────────────────────────┐
│    Reverse the Spin Direction of the Fan Blades to      │─120
│      Rotate in the Second Rotational Direction          │
└─────────────────────────────────────────────────────────┘
                            ↓
┌─────────────────────────────────────────────────────────┐
│         Dispense Fluid onto the Fan Blades While        │─130
│              Rotating at the First Speed                │
└─────────────────────────────────────────────────────────┘
                            ↓
┌─────────────────────────────────────────────────────────┐
│      Increase the Rotational Spin Rate to the Second    │─140
│                         Speed                           │
└─────────────────────────────────────────────────────────┘
                            ↓
┌─────────────────────────────────────────────────────────┐
│       Increase the Rotational Spin Rate to the Third    │─150
│                         Speed                           │
└─────────────────────────────────────────────────────────┘
                            ↓
┌─────────────────────────────────────────────────────────┐
│         Apply a Vacuum to Consolidate the Fluid into    │─160
│                    a Collection Vessel                  │
└─────────────────────────────────────────────────────────┘
                            ↓
┌─────────────────────────────────────────────────────────┐
│           Perform Additional Passes, if Necessary       │─170
└─────────────────────────────────────────────────────────┘
```

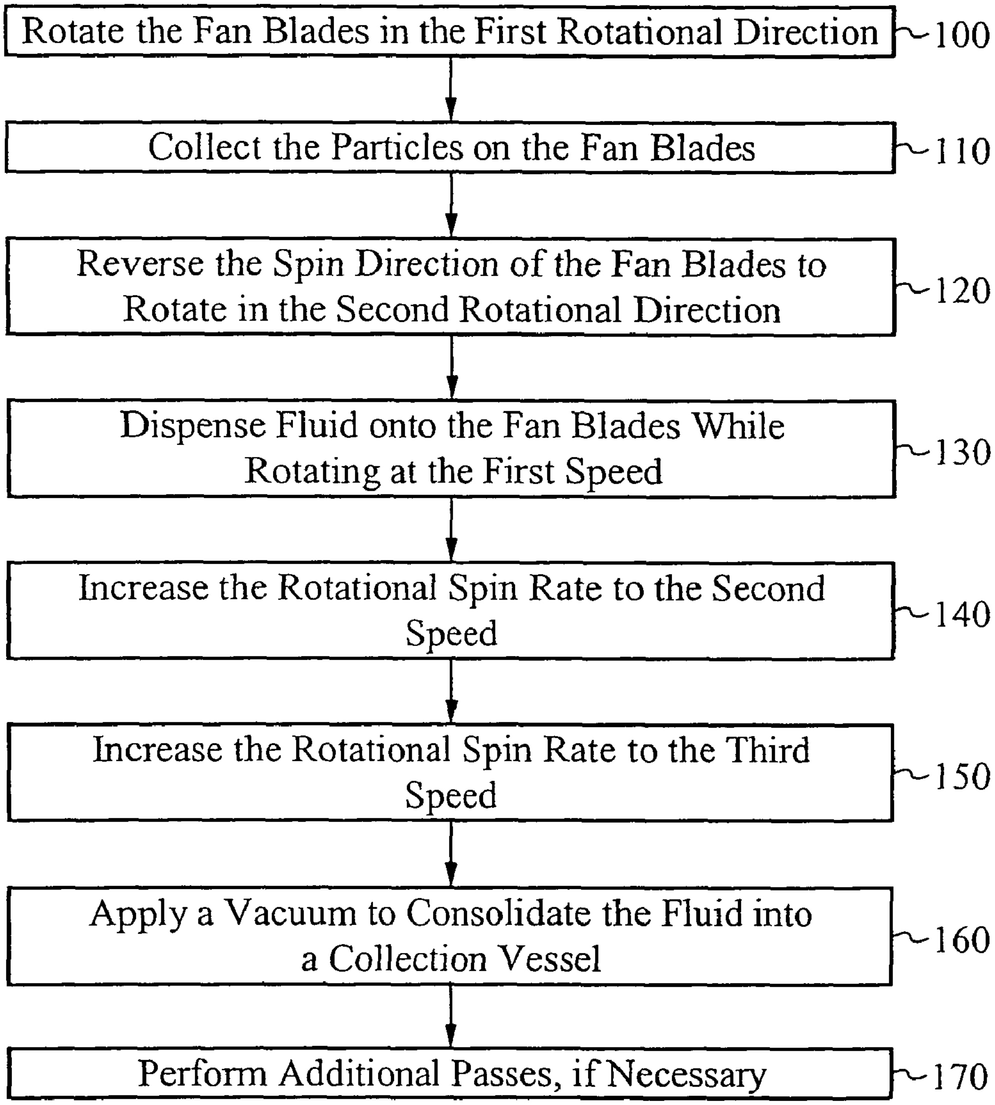

Fig. 7

AUTOMATED PARTICLE COLLECTION OFF OF FAN BLADES INTO A LIQUID BUFFER

FIELD OF THE INVENTION

The invention relates to a method of and apparatus for collecting particulates. More particularly, the invention relates to collecting air particles into a liquid buffer.

BACKGROUND OF THE INVENTION

Bio-threat detectors are used to monitor the ambient air to detect the presence of potentially harmful pathogens. In general, air is drawn into a detection apparatus, or trigger, where the particulates in the air are evaluated. Airflow into the detection apparatus is typically generated by a fan within the apparatus. The trigger continuously monitors the air and the individual molecules within a given airflow. Some triggers use lasers to scan the air path to interrogate the particles passing through. A harmless particle, such as a dust particle, can be discriminated from a harmful particle, for example an anthrax spore, because each different type of particle reflects a different wavelength of light. The laser light reflected of the passing particles is matched to database of known harmful wavelengths. When a harmful wavelength is detected, the trigger signals that a potential pathogen is present. However, the specific type of particle is not identified by the trigger.

A confirmation module takes over once the trigger signals the presence of a possible pathogen. The trigger signal initiates the confirmation module into action. The confirmation module identifies the particles detected by the trigger. Conventionally, when the trigger goes off, the potential pathogen is collected and taken to a lab where the confirmation module performs the analysis. Some detection apparatuses are configured with a secondary fan assembly, such as a muffin fan, such that the potential pathogens collect on the fan blades of the secondary fan assembly as the air flows through the detection apparatus. In such configurations, the secondary fan assembly is activated via the trigger signal. The fan blades or the fan assembly is removed from the detection apparatus and taken to a laboratory for analysis. At the lab, a swab is used to wipe the particles from the fan blade surface, or a solution is manually applied to the fan blades to elute the particles off the fan blade surface. This is a time-consuming process that is impractical for real-time threat assessment.

SUMMARY OF THE INVENTION

A particle collection apparatus is configured to collect airborne particles into a liquid solution. In some embodiments, the particles are collected from an airflow provided by an air collector and/or a particle detection apparatus. The particle collection apparatus includes a fan assembly, for example a muffin fan, and in some embodiments a fluid collector apparatus. The fluid collector apparatus is coupled to a collection vessel via one or more drain lines.

Fan blades within the fan assembly are rotated in a first rotational direction, thereby generating airflow from above the fan blades downward past the fan blades. The airborne particles adhere to the surface of the fan blades, hub, and fan housing as the air flows past. In this manner, particles are collected on the surfaces of the fan for a predetermined period of time. When the particle collection is completed, the fan direction is reversed to a second rotational direction and maintained at a relatively low rotational rate.

A fluid, such as a rinse buffer, is slowly dispensed onto the hub of the fan blades. Due to the centripetal force of the spinning fan blades, the fluid is spread thin across the top surface of the fan blades and the liquid film washes the blade of the fan, removing particulates from the fan blade. The solution is pushed outward against the inner wall of the fan housing forming a fluid meniscus.

The fluid meniscus is contained between the spinning fan blades and the inner wall of the fan housing. The fluid surface tension and the upward airflow caused by the fan blades rotating in the second rotational direction prevents the fluid meniscus from dripping downward.

Once the fluid is forced against the inner wall of the fan housing to form the fluid meniscus, the fan speed is increased in the second rotational direction. The centripetal force from the fan blades pushes the fluid contained in the fluid meniscus over the fan housing wall and into an annular reservoir of the fluid collector apparatus. The collected fluid is then vacuumed and consolidated into the collection vessel, where it can be subsequently analyzed.

In some embodiments, the fluid collector apparatus is eliminated and drain holes are drilled directly into the wall of the fan housing. The drains holes are positioned proximate to the outer edges of the fan blades. Drain lines are connected to the drain holes. The fluid, or fluid meniscus if one is formed, drains through the drain holes into the drain lines, and is consolidated in the collection vessel.

BRIEF DESCRIPTION OF THE DRAWINGS

FIG. 7 illustrates a method of operating the particle collection apparatus.

Embodiments of the particle collection apparatus are described relative to the several views of the drawings. Where appropriate and only where identical elements are disclosed and shown in more than one drawing, the same reference numeral will be used to represent such identical elements.

DETAILED DESCRIPTION OF THE PRESENT INVENTION

Figure 1:
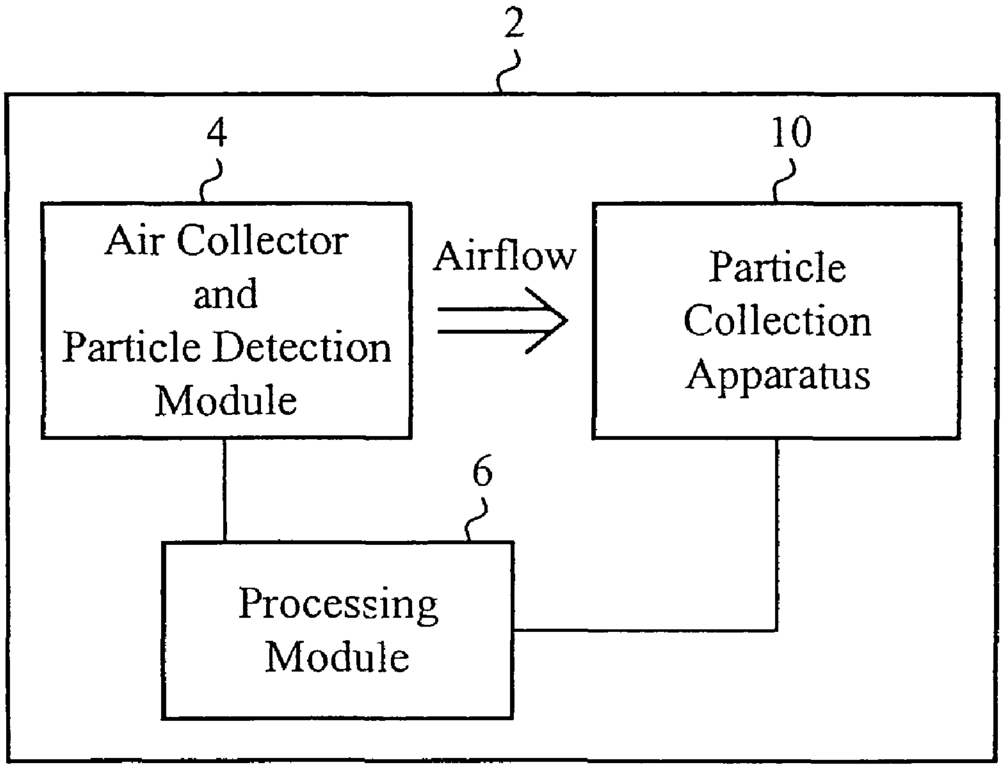
FIG. 1 illustrates a block diagram of an exemplary detection system.

FIG. 1 illustrates a block diagram of an exemplary detection system 2. The detection system 2 includes an air collector and particle detection module 4, a processing module 6, and a particle collection apparatus 10. The air collector and particle detection module 4 intakes air from the ambient and measures particular characteristics of the particles within the air, for example the reflectance characteristics. The processing module 6 is configured to provide automated control of the air collector and particle detection module 4 and the particle collection apparatus 10. The processing module 6 also receives the measured characteristics from the air collector and particle detection module 4 and determines if the measured characteristics match predetermined thresholds. For example, the processing module determines if measured reflectance corresponds to a specific wavelength of light. A trigger signal is generated by the processing module 6 if the measured characteristics match the predetermined thresholds. The trigger signal activates the particle collection apparatus 10. In one embodiment, the particle collection apparatus 10 is integrated within the detection system 2, as is shown in FIG. 1. Alternatively, the particle collection apparatus 10 is a separate unit from the detection system, and the particle collection apparatus 10 is coupled to the detection system such that air passing through the detection system is directed to the particle collection apparatus 10, such as via an air duct, when the trigger signal is generated.

Figure 2:
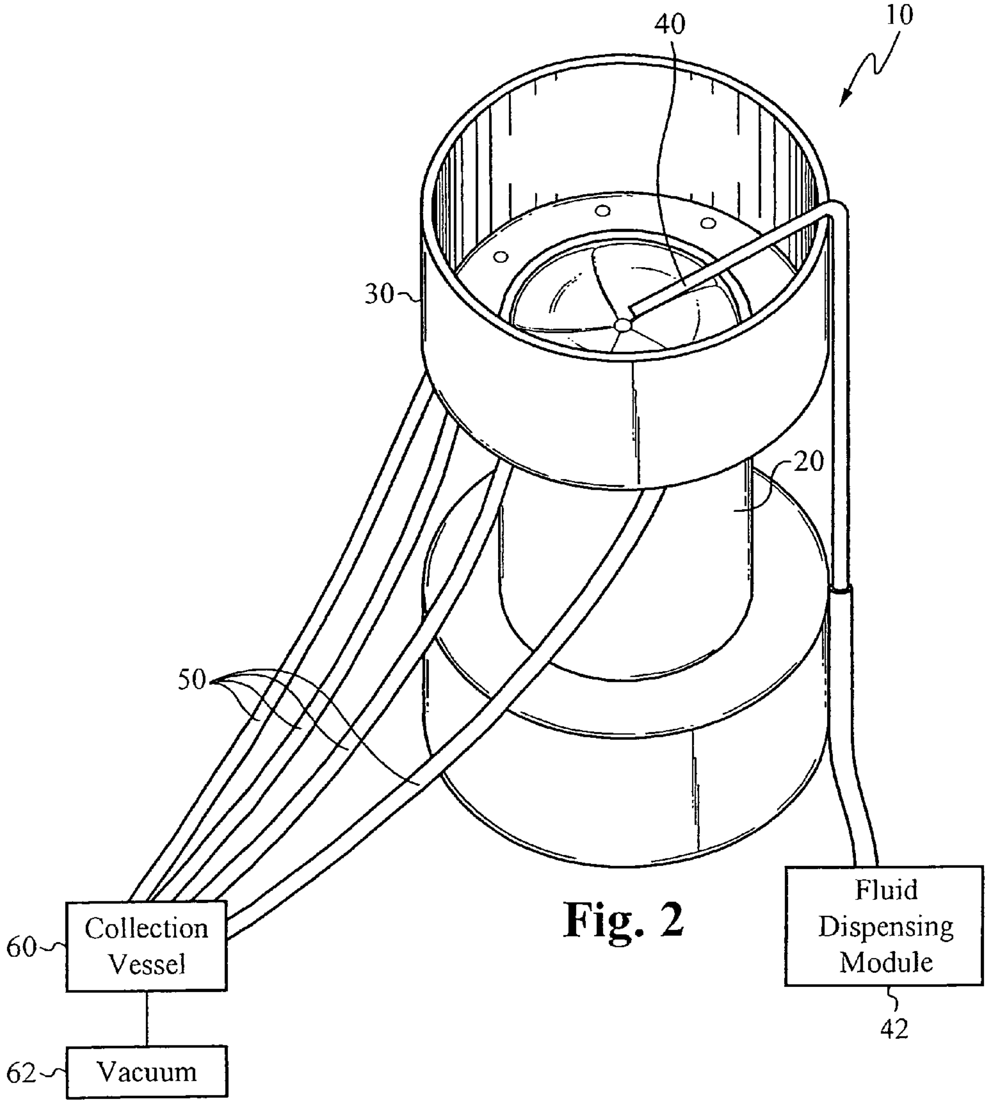
FIG. 2 illustrates a perspective view of the particle collection apparatus according to a first embodiment of the present invention.

FIG. 2 illustrates a perspective view of the particle collection apparatus 10 according to a first embodiment of the present invention. The particle collection apparatus 10 includes a fan assembly 20, a fluid collector 30, a fluid dispensing tube 40, a fluid dispensing module 42, one or more drain tubes 50, a collection vessel 60, and a vacuum 62.

Figure 3:
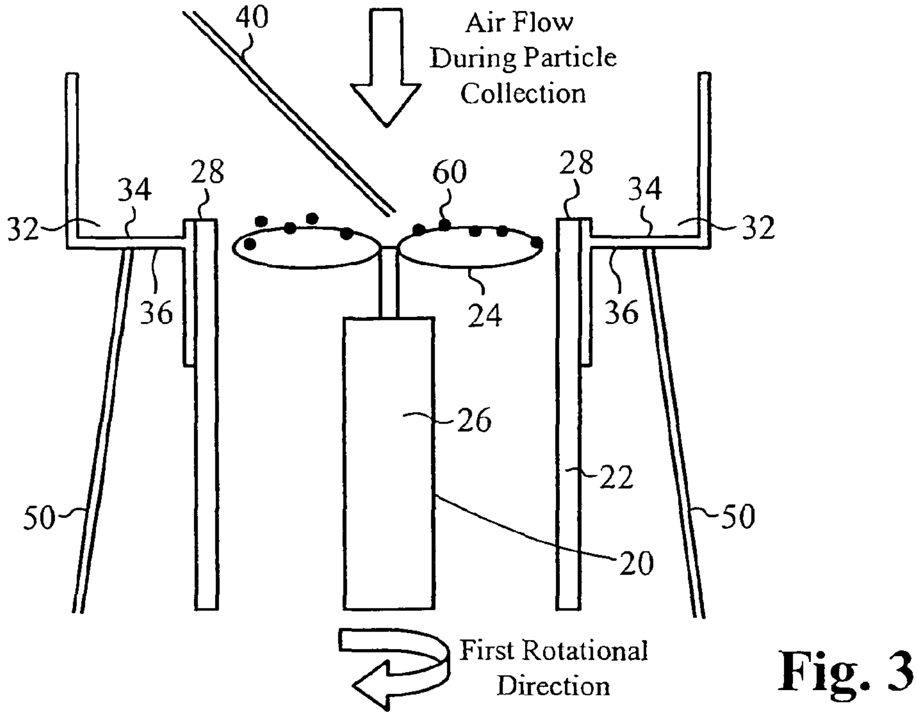
FIG. 3 illustrates a cut-out side view of the particle collection apparatus.

FIG. 3 illustrates a cut-out side view of the particle collection apparatus 10. The fan assembly 20 includes fan blades 24 coupled to a fan motor 26 within a fan housing 22. The fan housing 22 includes an upper rim 28 within which the fan blades 24 rotate. The fluid collector 30 is coupled to the fan housing 22 such that a reservoir 32 within the fluid collector 30 is positioned below the upper rim 28. In one embodiment, the reservoir 32 is configured as an annular reservoir positioned at the outer perimeter of the upper rim 28. A bottom surface 36 of the reservoir 32 includes one or more holes 34. A drain tube 50 is coupled to each hole 34.

The particle collection apparatus 10 is shown in FIG. 3 while in a first phase of operation. When first activated by the trigger signal, the fan motor 26, and therefore the fan blades 24, rotate in a first rotational direction, thereby drawing air from the air collector and particle detection module 4 through the fan assembly 20.

The fan blades 24 are configured such that when rotated in the first rotational direction, airflow is generated in a direction from the air collector and particle detection module 4 towards the top surface of the fan blades 24. In relation to FIG. 3, rotating the fan blades 24 in the first rotational direction, which in this case is clockwise, causes the airflow to move from the top of the page above the fan blades 24, down past the fan blades 24 As the airflow moves past the fan blades 24, particles 60 within the airflow accumulate on the top surface of the fan blades 24.

Under control of the processing module 6, the fan motor 26 rotates in the first rotational direction for an amount of time and a rotational speed sufficient for a detectable amount of particles 60 to collect on the fan blades 24. This amount of time and rotational speed is predetermined. After the predetermined amount of time, a second phase of operation is performed in which the rotational direction of the fan motor 26 is reversed to a second rotational direction at a rotational speed reduced relative to the rotational speed in the first direction.

Figure 4:
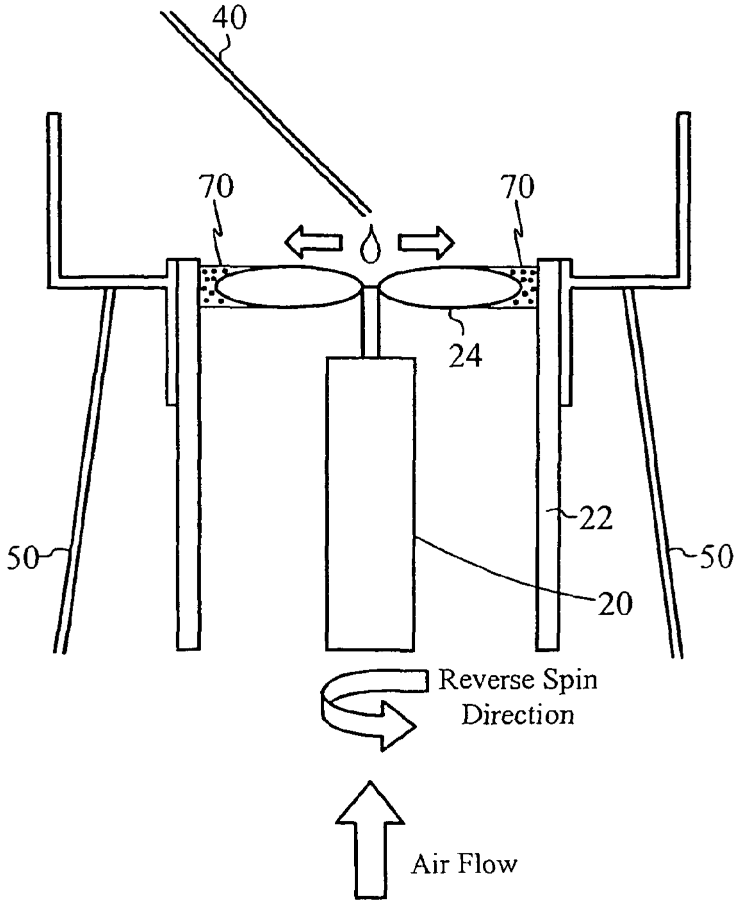
FIG. 4 illustrates the particle collection apparatus in the second phase of operation.

FIG. 4 illustrates the particle collection apparatus 10 in the second phase of operation. While in the second phase, the fan motor 26, and therefore the fan blades 24, rotate in the second rotational direction, which in this case is counter-clockwise. As a result, the airflow is reversed, moving from the bottom up as related to FIG. 4.

The fluid dispensing tube 40 dispenses fluid from the fluid dispensing module 42 onto the fan blades 24. In some embodiments, the fluid is water or water-based. Alternatively, the fluid is any fluid that does not damage the particles 60. The fluid dispensing module 42 regulates the amount of fluid that is dispensed by the fluid dispensing tube 40. The fluid is dispensed onto the center, or hub, of the fan blades 24. Due to the centripetal force of the rotating fan blades 24, the fluid spreads from the center of the fan blades 24 toward the out edge of the fan blades 24, thereby providing a liquid film over the top surface of the fan blades 24. During this step, the second rotational direction is maintained at a first speed. The first speed is low enough that the fluid maintains contact with the fan blades, but high enough that the fluid does not fly off the fan blades.

The speed in the second rotational direction is then increased to a second speed. The increased speed results in increased centripetal force applied to the fluid on the fan blades 24. This increased centripetal force forces the fluid to move to the outer edge of the fan blades 24, in the process removing collected particulates from the surface of the fan blades 24. In this manner, a wiping action is performed, whereby the particles accumulated on the surface of the fan blades are wiped off by centripetal force applied to the fluid.

The fluid is pushed outward against an inner wall of the fan housing 22, thereby forming a fluid meniscus 70. The fluid meniscus 70 is contained between the outer edges of the spinning fan blades 24 and the inner wall of the fan housing 22. By rotating the fan blades at the proper second speed, the upward airflow caused by the fan blades rotating in the second rotational direction along with the fluid surface tension substantially prevents the fluid meniscus 70 from dripping downward. As such, the second speed is low enough that the fluid does not fly off the fan blades 24, but the second speed is high enough to force the fluid to the inner wall of the fan housing 22 and high enough to generate sufficient upward airflow to form the fluid meniscus 70 and prevent the fluid from dripping downward off the fan blades 24.

In some embodiments, the second phase of operation is performed using a single speed, instead of the first speed and the second speed as described above. The single speed is low enough to prevent fluid from flying off the fan blades 24, but high enough to force the fluid to the inner wall of the fan housing 22 and to form the fluid meniscus 70.

Figure 5:
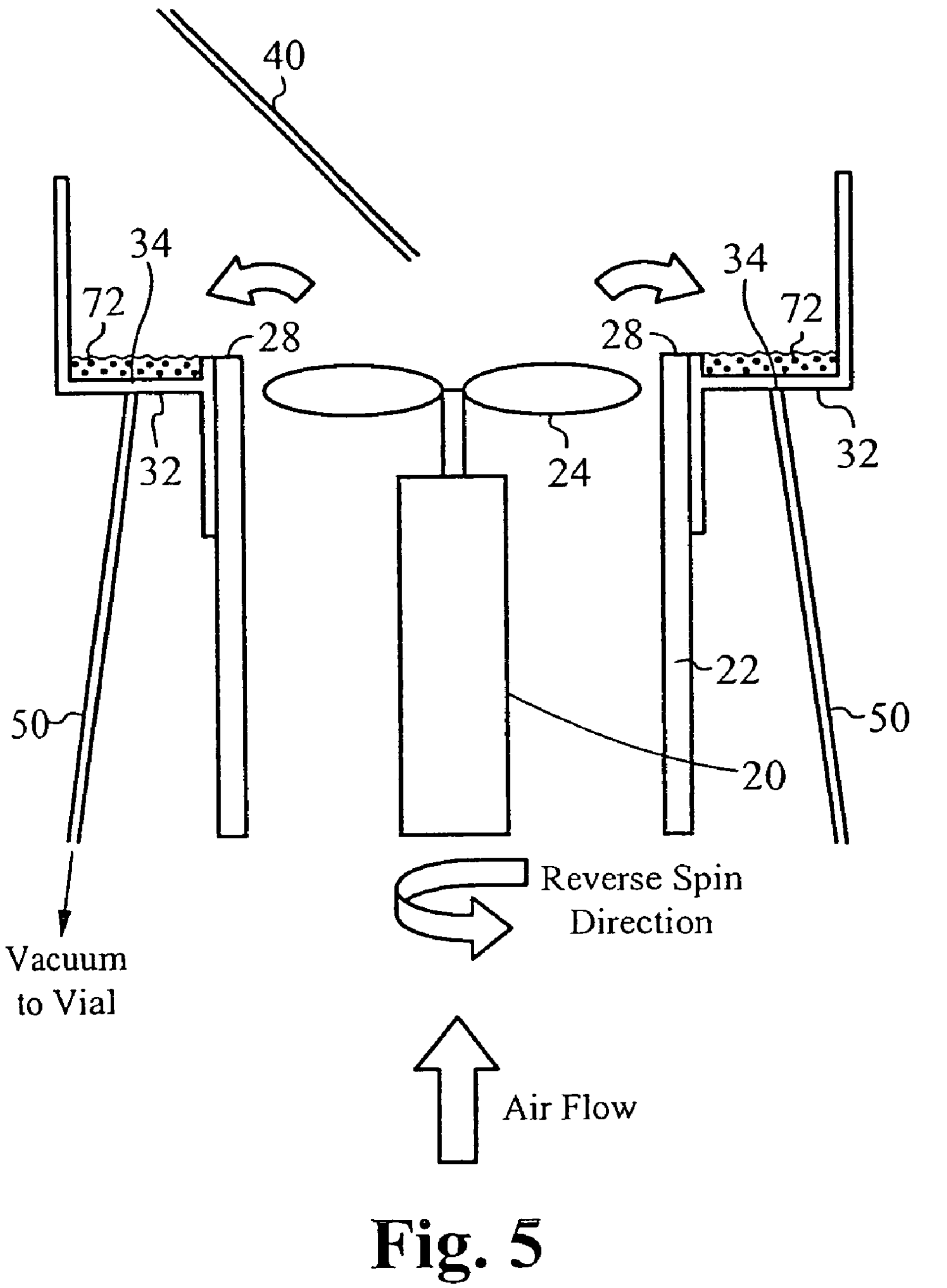
FIG. 5 illustrates the particle collection apparatus in a third phase of operation.

FIG. 5 illustrates the particle collection apparatus 10 in a third phase of operation. In the third phase, the speed in the second rotational direction is increased to a third speed. The third speed generates centripetal force sufficient to force the fluid in the fluid meniscus 70 over the upper rim 28 of the fan housing 22 and into the reservoir 32 of the fluid collector 30. As a result, the fluid 72 collects in the reservoir 32. The fluid collector 30 is composed of a hydrophobic material such that fluid contacting the wall of the fluid collector 30 settles in the reservoir 32. Alternatively, the fluid collector 30 is composed of any non-absorbent material.

Vacuum is applied to the drain tubes 50 by the vacuum 62 so that the fluid collected in the reservoir 32 is drawn through the holes 34, into the drain tubes 50, and into the collection vessel 60. In one embodiment, vacuum is applied to the drain tubes 50 when the fan motor 26 is increased to the third speed at the onset of the third phase. Alternatively, vacuum is applied to the drain tubes 50 during the second phase and the third phase of operation. Still alternatively, vacuum is applied to the drain tubes 50 any time the fan motor 26 rotates in the second rotational direction.

A single pass is referred to as performing the first phase, the second phase, and the third phase of operation. One or more passes can be performed to collect a larger percentage of the particles from the fan blades 24 and/or to increase the fluid sample size collected in the collection vessel 60. A maximum amount of fluid that can be dispensed onto the fan blades 24 during each pass is determined by the dimensions of the fan blade assembly 20, the material of the fan blades 24 and the fan housing 22, the viscosity and surface tension of the fluid, and the speeds necessary to perform the second operation and the third operation. If the amount of fluid dispensed onto the fan blades 24 exceeds the maximum amount, then the fluid meniscus 70 does not properly form and a significant portion of the fluid flows off the fan blades 24 and into the fan housing 22. This fluid, and the particles contained therein, are lost and unable to be collected in the fluid collector 30.

Figure 6:
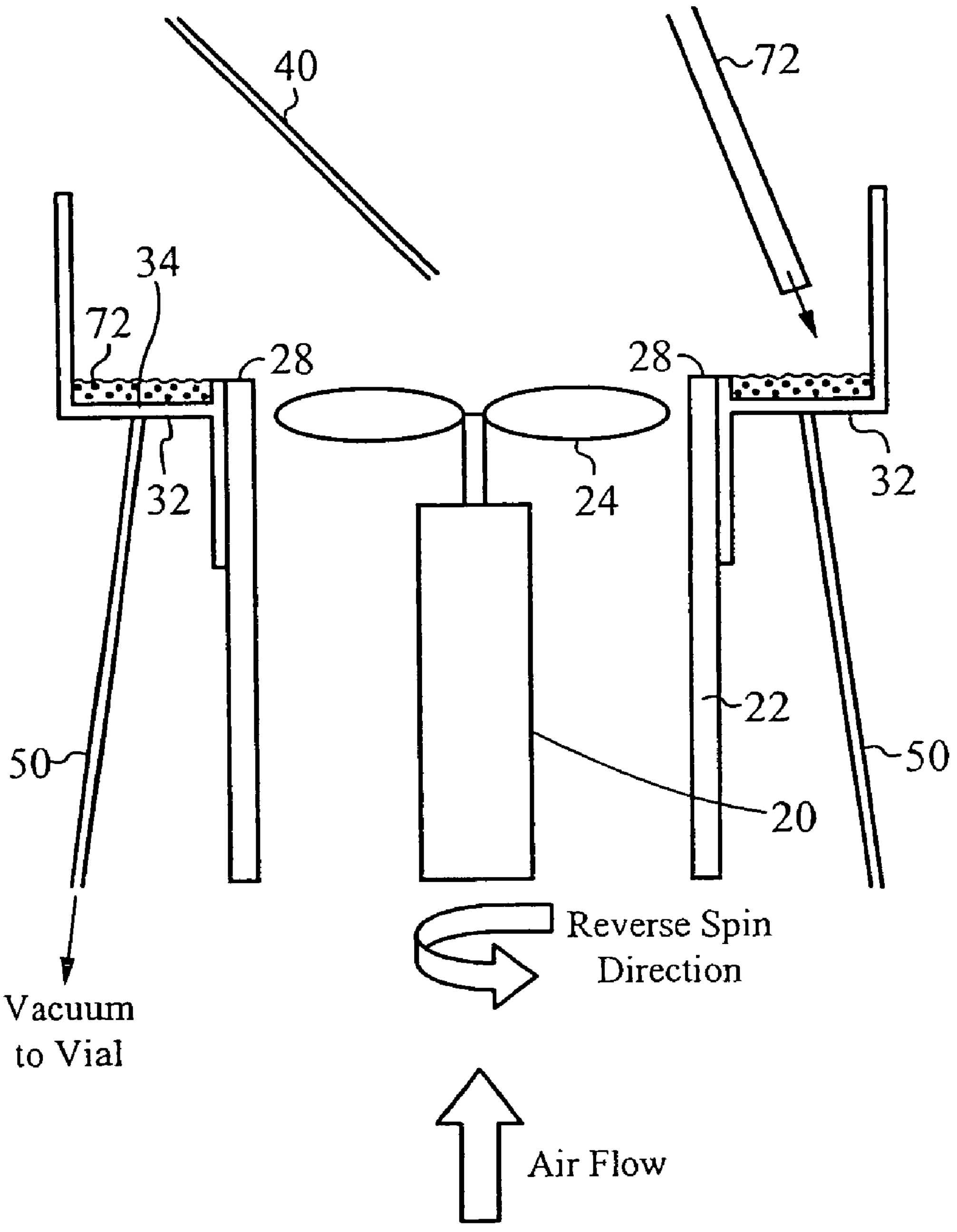
FIG. 6 illustrates the particle collection apparatus including a compressed air nozzle.

FIG. 6 illustrates the first embodiment of the particle collection apparatus 10 including a compressed air nozzle 72. The compressed air nozzle 72 is positioned at an angle to the reservoir 32 such that air output from the air nozzle 72 generates a vortex within the reservoir 32. The air forces fluid trapped between drain holes toward adjacent drain holes. In this manner, residual fluid in the reservoir 32 is pushed towards proximate holes 34.

FIG. 7 illustrates a method of operating the particle collection apparatus 10. At the step 100, the fan blades 24 are rotating in the first rotational direction. Rotating the fan blades 24 in the first rotational direction generates an airflow from above the fan blades 24 towards the fan blades 24. At the step 110, particles within the airflow are collected on the fan blades. As the airflow generated at the step 100 flows past the fan blades 24, particles within the airflow adhere to the surface of the fan blades 24. At the step 120, the spin direction of the fan blades 24 is reversed such that the fan blades are rotating in the second rotational direction. Rotation of the fan blades 24 in the second rotational direction generates an airflow from beneath the fan blades 24 toward the fan blades 24. The rotational spin rate of the fan blades 24 in the second rotational direction is set to a first speed. At the step 130, fluid is dispensed onto a hub of the fan blades 24 while rotating at the first speed. The centripetal force generated while rotating at the first speed forces the fluid into a liquid film over the top surface of the fan blades 24. At the step 140, the rotational spin rate of the fan blades 24 in the second rotational direction is increased to a second speed. The additional centripetal force generated while rotating at the second speed forces the fluid and the particles on the surface of the fan blades 24 to the outer edges of the fan blades 24. A fluid meniscus is formed between the edge of the fan blades 24 an the inner wall of the fan housing 22. The fluid meniscus includes the fluid and the particles.

In an alternative embodiment, the step 120 and the step 140 are combined into a single step such that when the spin direction of the fan blades 24 is reversed to rotate in the second rotational direction, the rotational spin rate of the fan blades 24 in the second rotational direction is set to the second speed. In this alternative embodiment, the fluid is dispensed onto the fan blades 24 while the fan blades 24 are rotating at the second speed in the second rotational direction, and the fluid is forced to the edge of the fan blades 24 to form the fluid meniscus.

At the step 150, the rotational spin rate of the fan blades 24 in the second rotational direction is increased to a third speed. The additional centripetal force generated while rotating at the third speed forces the fluid meniscus over the upper rim 28 and into the fluid collector 30. At the step 160, a vacuum is applied to the drain tubes 50 that are coupled to the fluid collector 30. The vacuum draws the fluid collected in the fluid collector 30 through the drain tubes 50 and into the collection vessel 60. At the step 170, the step 130 through 160 are repeated as many times as deemed necessary to sufficiently elute the particles 60 from the surface of the fan blades 24.

The fan blades 24 are composed of any material to which one or more types of particles to be collected will adhere. In some embodiments, the fan blades are composed of plastic. Alternatively, the fan blades 24 are coated with any material to which one or more types of particles to be collected will adhere.

Figure 8:
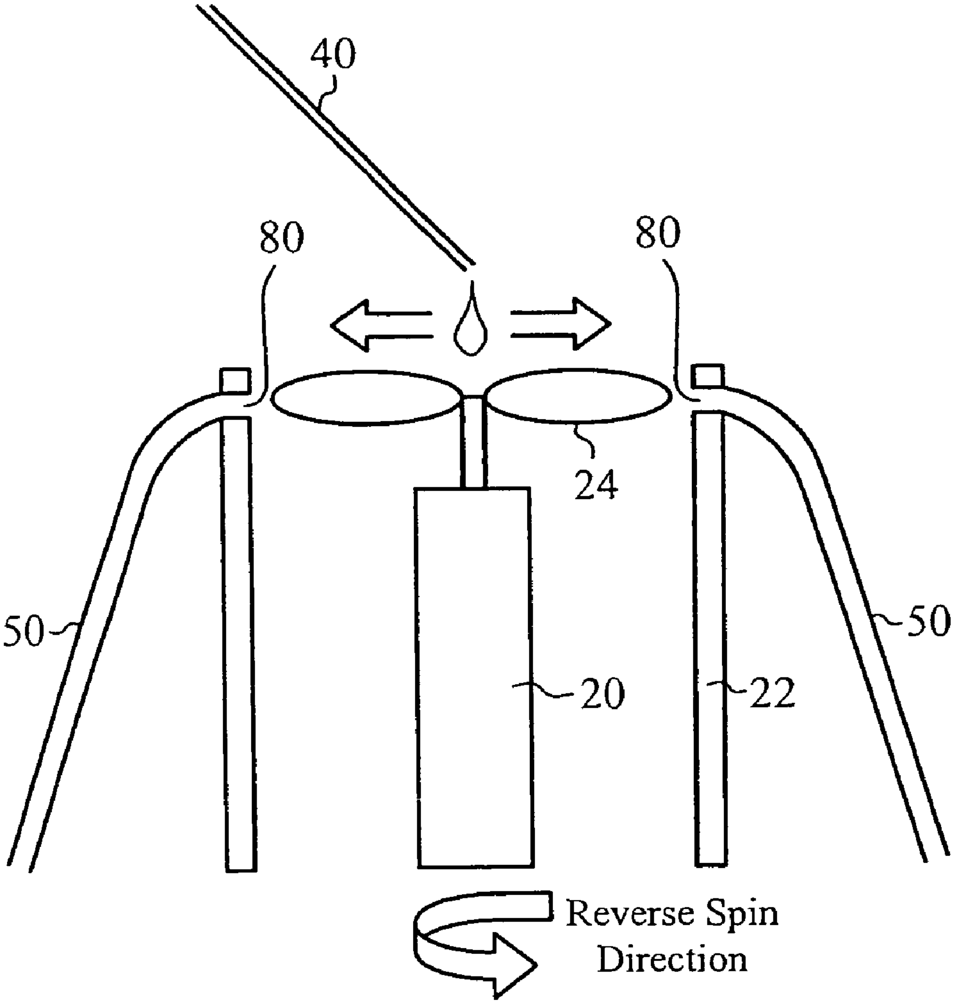
FIG. 8 illustrates a cut-out side view of a second embodiment of the particle collection apparatus.

FIG. 8 illustrates a cut-out side view of the particle collection apparatus according to a second embodiment of the present invention. In the second embodiment, the fluid collector 30 of the first embodiment is eliminated. Drain holes 80 are drilled through the wall of the fan housing 22 proximate to the fan blades 24. In some embodiments, the drain holes 80 are positioned substantially in the plane of the fan blades 24. Alternatively, the position of the drain holes 80 can be moved up or down relative to the plane of the fan blades so as to improve the collection of the fluid through the drain holes 80. One of the drain tubes 50 is coupled to each of the drain holes 80.

The second embodiment of the particle collection apparatus operates in two phases. The first phase is identical to the first phase of the first embodiment in which the fan motor 26 and the fan blades 24 rotate in the first rotational direction to collect particles on the fan blades 24. FIG. 8 illustrates the second embodiment of the particle collection apparatus in the second phase of operation. While in the second phase, the fan motor 26, and therefore the fan blades 24, rotate in the second rotational direction, which in this case is counter-clockwise. As a result, the airflow is reversed, moving from the bottom up as related to FIG. 8.

The fluid dispensing tube 40 dispenses fluid from the fluid dispensing module 42 onto the fan blades 24. The fluid is dispensed onto the center, or hub, of the fan blades 24. Due to the centripetal force of the rotating fan blades 24, the fluid is forced from the center of the fan blades 24 toward the inner wall of the fan housing 22, in the process removing collected particulates from the surface of the fan blades 24. The rotational speed during this second phase is low enough to prevent fluid from flying off the fan blades 24, but high enough to force the fluid to the inner wall of the fan housing 22.

Vacuum is applied to the drain tubes 50 by the vacuum 62 so that the fluid forced toward the inner wall of the fan housing 22 is drawn through the drain holes 80, into the drain tubes 50, and into the collection vessel 60. Vacuum is applied to the drain tubes 50 during the second phase of operation. One or more passes can be performed to collect a larger percentage of the particles from the fan blades 24 and/or to increase the fluid sample size collected in the collection vessel 60.

In some embodiments, the second phase is performed using two separate steps. During the first step, the fluid is dispensed onto the fan blades 24 and spreads from the center of the fan blades toward the outer edge of the fan blades, thereby providing a liquid film over the top surface of the fan blades 24. During this step, the second rotational direction is maintained at a first speed. The first speed is low enough that the fluid maintains contact with the fan blades, but high enough that the fluid does not fly off the fan blades. The speed in the second rotational direction is then increased to a second speed. The increased speed results in increased centripetal force applied to the fluid on the fan blades 24. This increased centripetal force forces the fluid to move to the outer edge of the fan blades 24.

In some embodiments, vacuum is not applied to the drain lines 50 during this second phase. Instead, the fluid is pushed outward against the inner wall of the fan housing 22, thereby forming the fluid meniscus 70, as in the first embodiment. The fluid meniscus 70 is contained between the outer edges of the spinning fan blades 24 and the inner wall of the fan housing 22. By rotating the fan blades at the proper speed, the upward airflow caused by the fan blades rotating in the second rotational direction along with the fluid surface tension substantially prevents the fluid meniscus 70 from dripping downward. As such, the rotational speed is low enough that the fluid does not fly off the fan blades 24, but the second speed is high enough to force the fluid to the inner wall of the fan housing 22 and high enough to generate sufficient upward airflow to form the fluid meniscus 70 and prevent the fluid from dripping downward of the fan blades 24. Subsequent to forming the fluid meniscus 70, and while maintaining rotation of the fan blades 24 in the second rotational direction, vacuum is applied to the drain lines 50 and the fluid meniscus 70 drains through the drain holes 80. It is understood that a portion of the fluid meniscus 70 may drain through the drain holes 80 prior to application of the vacuum.

Figure 9:
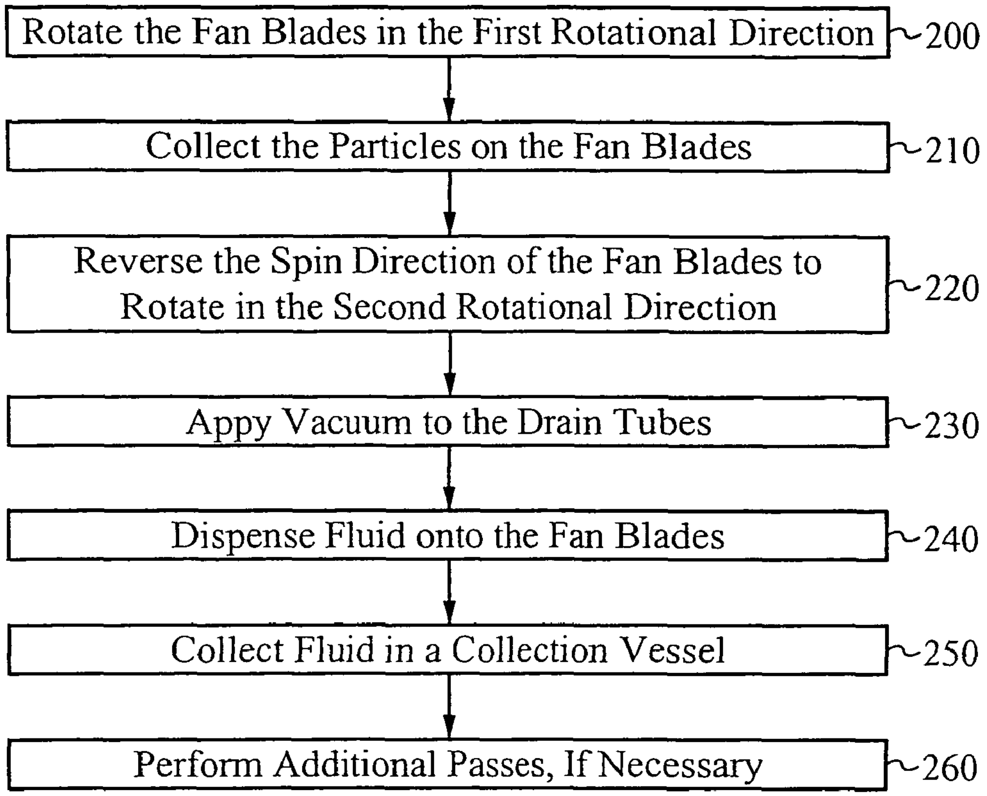
FIG. 9 illustrates a method of operating the second embodiment of the particle collection apparatus.

FIG. 9 illustrates a method of operating the second embodiment of the particle collection apparatus 10. At the step 200, the fan blades 24 are rotating in the first rotational direction. Rotating the fan blades 24 in the first rotational direction generates an airflow from above the fan blades 24 towards the fan blades 24. At the step 210, particles within the airflow are collected on the fan blades 24. As the airflow generated at the step 200 flows past the fan blades 24, particles within the airflow adhere to the surface of the fan blades 24. At the step 220, the spin direction of the fan blades 24 is reversed such that the fan blades are rotating in the second rotational direction. Rotation of the fan blades 24 in the second rotational direction generates an airflow from beneath the fan blades 24 towards the fan blades 24. At the step 230, a vacuum is applied to the drain tubes 50 that are coupled to the drain holes 80. At the 240, fluid is dispensed onto a hub of the fan blades 24 while rotating in the second rotational direction. The centripetal force generated while rotating in the second rotational direction forces the fluid and the particles on the surface of the fan blades 24 to the outer edges of the fan blades 24 and to the inner wall of the fan housing 22. At the step 250, the vacuum applied to the drain tubes 50 draws the fluid forced toward the inner wall of the fan housing 22 through the drain holes 80, the drain tubes 50 and into the collection vessel 60. At the step 260, the step 240 through 250 are repeated as many times as deemed necessary to sufficiently elute the particles 60 from the surface of the fan blades 24.

In an alternative embodiment, the step 230 is performed after the step 240. In this manner, vacuum is not applied to the drain tubes 50 until after a fluid meniscus is formed between the edge of the fan bladed 24 and the inner wall of the fan housing 22.

The particle collection apparatus 10 is automated to collect a fluid sample that includes the particles eluted from the surface of the fan blades. The processing module 6 controls the automated functions associated with performing the first phase, the second phase, and the third phase described above. In this manner, airborne particles can be automatically collected into a liquid solution. In alternative embodiments, operation of the particle collection apparatus can be manually performed, either in part or in full.

As described herein, the term “speed” is a relative term. The third speed is faster than the second speed, and the second speed is faster than the first speed. Each of the actual speeds is dependent on many factors, including but not limited to, the size of the fan blades, the amount of fluid dispensed onto the fan blades, the distance between the outer perimeter of the fan blades and the inner wall of the fan housing, the height of the fan housing rim relative to the fan blades, and the type of fluid used. For a specific fan assembly and fluid, the actual first speed, second speed, and third speed are experimentally determined.

The particle collection apparatus is described above in relation to a bio-threat application. It is understood that the particle collection apparatus can also be used to collect non-harmful air particles and in general the particle collection apparatus can be used to collect any particles that collect on the surface of a fan blade. It is also understood that the particle collection apparatus can be used within a system, such as the bo-threat detection system described above, or the particle collection apparatus can be used as a stand alone device.

The present invention has been described in terms of specific embodiments incorporating details to facilitate the understanding of the principles of construction and operation of the invention. Such reference herein to specific embodiments and details thereof is not intended to limit the scope of the claims appended hereto. It will be apparent to those skilled in the art that modifications may be made in the embodiment chosen for illustration without departing from the spirit and scope of the invention.

What is claimed is:

1. A method of collecting airborne particles into a liquid solution, the method comprising:

a. rotating fan blades in a first rotational direction, thereby generating airflow past the fan blades in a first direction, wherein the airflow includes particles to be collected;

b. collecting the particles on the fan blades while rotating the fan blades in the first rotational direction;

c. rotating the fan blades in a second rotational direction at a first speed, thereby generating airflow past the fan blades in a second direction;

d. dispensing a fluid onto the fan blades while rotating the fan blades at the first speed, wherein the fluid and the particles are centripetally forced to the edge of the fan blades; and e. rotating the fan blades in the second rotational direction at a second speed, thereby forcing the fluid and the particles into a fluid collector.

2. The method of claim 1 further comprising forming a fluid meniscus of the fluid and particles forced to the edge of the fan blades, wherein the fluid meniscus is formed between the edge of the fan blades and an inner wall of a fan housing.

3. The method of claim 2 wherein the fluid meniscus is formed by a surface tension of the fluid and the airflow moving in the second direction.

4. The method of claim 3 wherein the second direction is perpendicular to the fan blades.

5. The method of claim 1 further comprising generating a trigger signal, wherein the trigger signal initiates rotating the fan blades in the first rotational direction.

6. The method of claim 1 further comprising:

a. coupling one or more drain lines to the fluid collector; and b. applying a vacuum to the one or more drain lines to draw the fluid from the fluid collector into a collection vessel.

7. The method of claim 6 further comprising blowing air across the fluid collector to force residual fluid toward the one or more drain line.

8. The method of claim 1 wherein rotating the fan blades at the first speed, dispensing the fluid onto the fan blades, and rotating the fan blades at the second speed comprises a single pass, and the method further comprises performing multiple passes.

9. The method of claim 1 further comprising rotating the fan blades in the second rotational direction at a third speed, thereby spreading the fluid across the fan blades, wherein the third speed is slower than the first speed and the second speed.

10. An apparatus to collect airborne particles into a liquid solution, the apparatus comprising:

a. a fan assembly including a fan motor coupled to one or more fan blades, wherein the fan motor and the one or more fan blades are configured to rotate in a first rotational direction thereby generating airflow past the fan blades in a first direction that is perpendicular to a plane of rotation of the one or more fan blades, wherein the airflow includes particles that adhere to the fan blades, and to rotate in a second rotational direction thereby generating airflow past the fan blades in a second direction that is opposite the first direction, further wherein the fan assembly further comprises a fan housing including an upper rim, the upper rim is positioned proximate to an outer edge of the one or more fan blades;

b. a fluid dispensing tube configured to dispense fluid onto a hub of the fan blades while the fan motor is rotating in the second rotational direction, thereby forcing the fluid and the particles to an outer edge of the fan blades; and c. a fluid collector coupled to the upper rim of the fan assembly to collect the fluid and particles forced from the fan blades.

11. The apparatus of claim 10 wherein the fluid collector includes one or more holes, each hole coupled to a drain line, and the apparatus further comprises a collection vessel coupled to the drain lines.

12. The apparatus of claim 11 further comprising a vacuum coupled to the collection vessel to apply vacuum to the drain lines.

13. The apparatus of claim 10 further comprising an air nozzle configured to direct air across the fluid collector to force residual fluid toward the one or more holes.

14. The apparatus of claim 10 wherein the fluid dispensing tube is positioned to dispense fluid onto a hub of the fan blades.

15. The apparatus of claim 10 wherein the fan motor is configured to operate at a first speed, a second speed, and a third speed in the second rotational direction, wherein the third speed is faster than the second speed, and the second speed is faster than the first speed.

16. The apparatus of claim 15 wherein the fan motor is configured to operate at the first speed while dispensing fluid onto the fan blades, to operate at the second speed to force the fluid and the particles to the outer edge of the fan blades, and to operate at the third speed to force the fluid and particles into the fluid collector.

17. The apparatus of claim 10 wherein the fan motor is configured to operate at a first speed and a second speed in the second rotational direction, wherein the second speed is faster than the first speed.

18. The apparatus of claim 17 wherein the fan motor is configured to operate at the first speed while dispensing fluid onto the fan blades and to force the fluid and the particles to the outer edge of the fan blades, and to operate at the second speed to force the fluid from the outer edge of the fan blades into the fluid collector.

19. The apparatus of claim 10 wherein the fluid collector includes a reservoir, further wherein the fluid collector is coupled to the fan assembly such that the reservoir is positioned below a level of the upper rim.

20. The apparatus of claim 10 further comprising a fluid dispensing module to regulate the fluid dispensed from the fluid dispensing tube.

21. The apparatus of claim 20 further comprising a processing module coupled to the fan assembly and to the fluid dispensing module to automatically operate the apparatus.

22. The apparatus of claim 10 wherein the fan blades comprise a material to which the particles adhere.

23. The apparatus of claim 10 wherein the fan blades including a coating comprised of a material to which the particles adhere.

24. A method of collecting airborne particles into a liquid solution, the method comprising:

a. rotating fan blades in a first rotational direction, thereby generating airflow past the fan blades in a first direction, wherein the airflow includes particles to be collected;

b. collecting the particles on the fan blades while rotating the fan blades in the first rotational direction;

c. rotating the fan blades in a second rotational direction, thereby generating airflow past the fan blades in a second direction;

d. dispensing a fluid onto the fan blades while rotating the fan blades in the second direction, wherein the fluid and the particles are centripetally forced towards and off the edge of the fan blades; and e. collecting the fluid and the particles forced off the edge of the fan blades.

25. The method of claim 24 wherein rotating the fan blades in the second rotational direction and dispensing the fluid onto the fan blades comprises a single pass, and the method further comprises performing multiple passes.

* * * * *